(12) United States Patent
Au et al.

(10) Patent No.: US 6,748,260 B2
(45) Date of Patent: Jun. 8, 2004

(54) HAND-HELD SURFACE ECG AND RF APPARATUS INCORPORATED WITH A MEDICAL DEVICE

(75) Inventors: Nelson Au, Foster City, CA (US); Mark Brecht, Imperial Beach, CA (US); Marion Buchenau, San Francisco, CA (US); Thomas Crowley, Lino Lakes, MN (US); David Karshmer, Menlo Park, CA (US); Chester G. Nelson, Maple Grove, MN (US); Nick Oakley, Portland, OR (US); Edwin M. Pearce, Jr., San Francisco, CA (US); Nancy Perry Pool, Minnetonka, MN (US); Richard M. Powell, Southport, NC (US); Elisha Tal, Maccabim (IL)

(73) Assignee: Medtronic, Inc., Minneapolis, MN (US)

( * ) Notice: Subject to any disclaimer, the term of this patent is extended or adjusted under 35 U.S.C. 154(b) by 447 days.

(21) Appl. No.: 09/821,201

(22) Filed: Mar. 29, 2001

(65) Prior Publication Data

US 2002/0095093 A1 Jul. 18, 2002

Related U.S. Application Data (60) Provisional application No. 60/192,943, filed on Mar. 29, 2000.

(51) Int. Cl.[7] ................................................. A61B 5/04
(52) U.S. Cl. ........................................ 600/509; 607/32
(58) Field of Search ................................. 600/509, 520, 600/519, 523, 372, 384, 382; 128/903; 607/30–32, 60; 482/8–9

(56) References Cited

U.S. PATENT DOCUMENTS

| | | | |
|---|---|---|---|
| 4,151,513 A | | 4/1979 | Menken et al. |
| 4,319,581 A | * | 3/1982 | Cutter .......................... 600/520 |
| 4,681,118 A | * | 7/1987 | Asai et al. ................... 600/387 |
| 5,289,824 A | | 3/1994 | Mills et al. |
| 5,345,362 A | | 9/1994 | Winkler |
| 5,350,411 A | | 9/1994 | Ryan et al. |
| 5,503,158 A | | 4/1996 | Coppock et al. |
| 5,511,553 A | * | 4/1996 | Segalowitz .................. 600/508 |
| 5,738,104 A | * | 4/1998 | Lo et al. ...................... 600/521 |
| 5,752,976 A | | 5/1998 | Duffin et al. |
| 5,752,977 A | | 5/1998 | Grevious et al. |
| 6,104,296 A | * | 8/2000 | Yasushi et al. .............. 340/576 |
| 6,167,310 A | | 12/2000 | Grevious |
| 6,280,396 B1 | * | 8/2001 | Clark .......................... 600/547 |
| 6,463,385 B1 | * | 10/2002 | Fry ............................. 701/213 |
| 6,497,638 B1 | * | 12/2002 | Shea .............................. 482/8 |

* cited by examiner

Primary Examiner—Mark Bockelman
(74) Attorney, Agent, or Firm—Girma Wolde-Michael; Paul H. McDowall (57) ABSTRACT

A hand-holdable structure implementing electrodes to enable good skin-electrode contact to acquire ECG readings is disclosed. Specifically, the structure is shaped to enable patients to apply a simple gentle grip to have a reliable skin-electrode contact and to automatically commence ECG tracing transmission to a patient monitoring station. In one embodiment the structure incorporates an RF telemetry head to simultaneously transfer IMD stored data in conjunction with the ECG tracings. The structure independently or in combination with the RF telemetry head is adaptable to a system of data communications with a programmer or equivalent instrument to transfer ECG and IMD data to a remotely located physician station or patient data storage server. The system is also adaptable for use with a web-enabled network such as, without limitation, the Internet, intranet, World Wide Web, extranet or equivalent.

18 Claims, 5 Drawing Sheets

HAND-HELD SURFACE ECG AND RF APPARATUS INCORPORATED WITH A MEDICAL DEVICE

This application claims the benefit of provisional application No. 60/192,943 filed Mar. 29, 2000.

FIELD OF THE INVENTION

This invention generally relates to a method and apparatus for detecting cardiac depolarizations for remote monitoring of electrocardiograms (ECGs) from patients with an implanted medical device (IMD). More particularly, this invention pertains to hand-held electrodes for recording and transmitting ECG data to a remote site for analysis by a physician, clinician, or diagnostician.

BACKGROUND OF THE INVENTION

Cardiac muscle is an excitable tissue and includes electrically excitable cardiac muscle cells. Typically, upon intrinsic or artificial supra-threshold electrical excitation, cardiac muscle cells generate a depolarization wave that triggers a delayed contraction. Cardiac muscle cells are electrically coupled enabling the flow of depolarization waves between them. Normally, a group of pacemaker cells located at the Sino-Atrial node in the right atrium originates the depolarization wave that then spreads rapidly to the rest of the heart, first to the atria and then to the ventricles. An ECG is the record of the cardiac depolarizations. A physician uses ECGs to determine a patient's cardiac conduction condition. Depending on the patient's medical condition, it may be needed to document the patient's status at times other than the patient's clinic visit or hospital stay. Typically and prior to the advent of remote monitoring capability, an ECG reading is taken only in a clinical or hospital environment.

Since a patient's skin exhibits voltage differences due to electrical depolarizations of the heart's muscle cells, ECG signal acquisition involves the use of two or more electrodes placed on a patient's skin. In a clinic, ECGs are recorded via a number of sensing electrodes. An individual electrode usually includes a metal contact that attaches to the patient's skin with an adhesive bandage on which a conductive gel is placed. When paired with other electrode(s), electrode pairs detect changes in electrical potential across the patient's skin. These signals represent cardiac depolarizations and are fed to a recorder that may store them or print them out on a roll of paper as ECG tracings. The ECG electrodes are also capable of detecting artifacts from IMDs such as those indicating a pacing output pulse and printing these on the resultant tracing.

As the technology associated with IMDs advanced, it soon became clear that it was necessary to have a remote ECG monitoring capability. Transtelephonic ECG monitoring soon became routine for patients with IMDs. Typically, such monitoring is short-term, and involves the patient contacting the physician by phone, and employing an ECG transmitter of the type described in U.S. Pat. No. 4,151,513, issued to Menken et al. Use of such a device, however, typically requires the patient to apply ECG electrodes to the body, and subsequently to couple the monitoring device to their telephone to allow for a brief period of monitoring.

Alternatively, U.S. Pat. No. 5,503,158 issued to Cuppock, et al describes an ambulatory ECG monitor with a number of sensors placed on the patient's skin to generate an ECG. An amplifier is connected to the sensors to generate an amplified signal. A remote processor is equipped with a receiver and is connected to the amplifier to receive and process the amplified signal to obtain the patient's electrocardiogram.

Other methods have also been described, for example, attaching electrodes to the wrist in U.S. Pat No. 5,289,824, issued to Mills et al, or one of the fingers of each hand. In the '824 patent, incorporated herein by reference in its entirety, a wrist-worn monitor is provided that, without external connections of any kind, enables local, multiple event ECG data recording and telecommunication to a remote site. The monitor is housed in a compact and lightweight housing and is operable whenever the patient simply places his/her hand over a portion of the monitor's face to contact an upper skin electrode. Circuitry is provided to drive an integral speaker for the telecommunication of the ECG signal or cardiac event data via telephone lines to a remote site for so-called "over-read", diagnosis and archival recording. The monitor's housing includes dual, integral dry skin electrodes located on a wrist contacting, inner or rear base plate and on an outer or front surface contactable by the palm of the patient's other hand.

Because the average age of the patients who receive an IMD is generally over seventy, the application and use of ECG electrodes often poses various operational and implementation issues. For example, in the '158 patent, multiple electrodes are placed on the patient's upper torso and remain there over a period of time. These attached electrodes may irritate the skin and make it difficult to take a shower. The wrist electrode, described is the '824 patent, eliminates the permanent application of electrodes while maintaining the ability to have a connection to a remote monitor as disclosed in the '158 patent. The wrist electrode, however, is not without its own problems. For example, an elderly patient may have arthritis and find it quite difficult to attach wrist electrodes or, due to very thin wrists, keep them in close contact with the skin.

Other types of electrodes, especially those intended for direct application to the skin, such as stick-on electrodes that require a conductive gel, are quite difficult for any patient to apply regardless of his or her age. Removing these types of electrodes can cause extreme skin irritation to a patient of any age, but especially to an elderly patient whose skin may likely be quite thin. Finally, positioning such electrodes requires training in order to acquire an adequate signal that result in an ECG of diagnostic quality.

Transtelephonic systems, known in the art, seem to require a number of connecting cables to attach the sensing electrodes to the monitoring device. The number of cables may increase when a separate RF head is provided to detect and transmit simultaneous data from the IMD. The responsibility to ensure an adequate connection of these cables to the monitor should not be left to patients. This is partly because patients may forget and, in most cases, may not be comfortable operating electronic equipment.

Accordingly, current patient management and follow-up require a nurse, clinician/technician call or inform the patient of the need for an ECG tracing when, for example, a physician may ask for one. This call may serve as a reminder to the patient that the appointment is scheduled for some time in the future. Such reminders are important because scheduled monitoring often occur infrequently, for example, at three or six month intervals.

Following the reminder, the patient must locate the equipment some time prior to the actual start of the scheduled monitoring. After connecting or applying the ECG electrodes, the patient must connect them to the monitoring device. If the monitoring device is a transtelephonic device, that device must also be plugged into a wall socket. The patient waits for the call from the nurse/technician and then begins to transmit the ECG, when instructed to do so. If the ECG electrodes do not have adequate contact with the skin or improperly positioned, the patient is instructed to reposition the ECG electrodes to try another transmission. The nurse/technician on the other end of the line can only hope the patient will reposition the electrodes properly. At times, many attempts are made without much success. In such cases, the only option is to schedule a clinic visit to ensure the acquisition of a diagnostic quality ECG tracing.

SUMMARY OF THE INVENTION

The present invention, inter alia, overcomes the various limitations of the prior art and simplifies the steps required to collect reliable medical data. Specifically, the present invention includes a cable onto which are attached two or three objects, at least two of which are hand-holdable structures that the patient grasps in the hand in addition to any optional lightweight RF telemetry head. The holdable structure incorporates ECG electrodes. These electrodes ensure good skin-electrode contact to detect cardiac depolarizations. The RF telemetry head is implemented to detect ECGs via electrodes and also downlink with an IMD if needed. When arranged in this manner, the RF telemetry head serves a dual role by detecting ECGs and/or collecting and transmitting data from the IMD. Specifically, when the telemetry head is used to detect depolarization potentials, surface ECG electrodes are incorporated into the telemetry head are used. In the alternative, the head could be used to collect data from the IMD, while simultaneous collecting depolarization data via the electrodes.

In another embodiment, the lightweight telemetry head may be used solely as a means of collecting IMD data. Generally, the head may collect continuous data from the holdable structures or stored data from the IMD. Preferably, a shielded cable RF/telemetry unit connects the holdable structures to the telemetry head. The RF/telemetry unit transmits ECGs and/or collected IMD data via any one of several means, hard-wired, RF telemetry, infra-red connectivity, BlueTooth or Home RF technology, transtelephonic, or other standard connector known in the art. The RF telemetry of the present invention is similar to telemetry systems disclosed in commonly assigned U.S. Pat. No. 6,167,310 to Grevious; U.S. Pat. No. 5,752,977 to Grevious et al. and U.S. Pat. No. 5,350,411 to Ryan et al. which patents are incorporated herein by reference in their entirety.

Because of the relatively advanced age of the average IMD patients, it is preferred to offer a system that takes into account the potential for some disability (e.g., arthritis) in addition to being user friendly. The present invention addresses such issues. Further, the present invention the use of gels by incorporating ECG electrodes in the holdable structure and/or telemetry head. These electrodes require only dry skin contact.

The present invention implements a hand holdable structure that allows an easy, natural grip to enable patients to apply a simple gentle grip on the structure to record ECGs. There is no need to use a band or other means to ensure a tight or forced grip. The design takes into account the possibility that an individual patient might have an impaired grip and may be unable to exert to a tight grip around the structure. The total weight of the structure and associated cable(s) and devices have been kept very light. Preferably, the cable weighs less than 2 pounds, to accommodate those patients who find it difficult to lift and support heavy weights.

Collection of ECG tracings automatically begins when the patient grasps the structure and the lightweight telemetry head maintains a good skin-electrode contact. When the telemetry head is in use to collect medical device data, grasping the structure with good skin-electrode contact automatically activates both ECG acquisition and data collection. Subsequently, as soon as the patient breaks skin-electrode contact, ECG acquisition and is terminated.

DETAILED DESCRIPTION OF THE DRAWINGS

Figure 1:
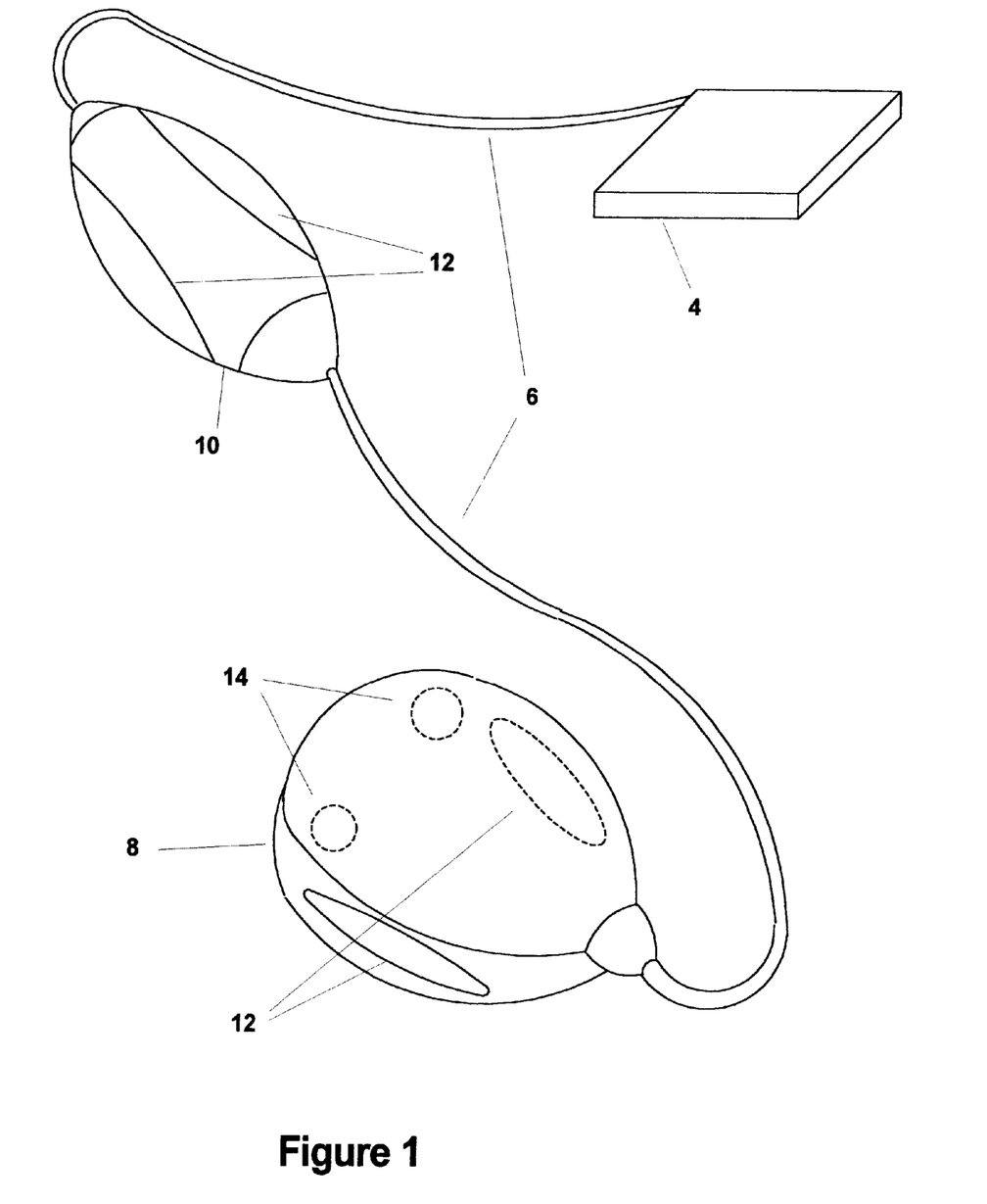
FIG. 1 is an illustration of a first embodiment, including a hand holdable structure connected to a lightweight telemetry head with both elements connected together by cable and then by cable to an ECG/RF telemetry unit.

FIG. 1 depicts a first embodiment of the present invention, wherein the patient is able to grasp structure 10 in one hand and lightweight telemetry head 8 in the other. Skin contact with one or more conductive, non-oxidizing electrodes 12 located on structure 10 and telemetry head 8 is achieved by virtue of a substantially ovoid bulb geometry of structure 10. More specifically, structure 10 is designed to provide ease of grasp and also enable intimate contact with a patient's hand to record and transmit ECG data Telemetry head 8 is adapted to a size and weight to fit comfortably in the hand of the patient. The patient's fingers or other parts of the hand will make contact with electrodes 12 on either side of structure 10 and telemetry head 8. Cable 6 serially connects telemetry head 8, structure 10, and telemetry unit 4. Telemetry unit 4 transmits ECGs and/or collected IMD data via any one of several data transmission systems, including but not limited to a modem, RF telemetry, infra-red connectivity, Blue Tooth, Home RF technology, transtelephonic systems or equivalent systems known in the art. Cable 6 is shielded in such a way that the RF data signals do not interfere with the ECG signals collected at structure 10. Cable 6 also has one connector with a sufficient number of pins to transfer both types of signals without interference.

Further referring to FIG. 1, the patient will usually be transmitting ECG signals as well as data from the IMD. Telemetry head 8 includes sensors 14 to enable data transmission from the IMD. Specifically, the patient positions telemetry head 8 over the IMD to initiate an uplink session in which stored data from the IMD is transmitted via telemetry 4. Similarly, ECG signals will be transmitted when structure 10 and 8 are properly positioned with good skin contact in the patient's hand.

Referring to structure 10 in more detail, the shape of electrodes 12 and the design of structure 10 may vary.

Specifically, the substantially ovoid bulbous shape of structure 10 depicted herein is only a representative sample of the many hand-holdable shapes and structures contemplated by the present invention. For example, the bulbous shape of structure 10 could be circular or may take the shape of any other geometry that can be fabricated to fit easily and comfortably into a patient's grasp or on/over the hand. Similarly the oblong shape of electrodes 12 could be varied to cover the whole surface of ovoid structure 10. Telemetry head 8, in this embodiment, may also be fabricated in other geometric shapes. The present invention serves to transmit ECGs and IMD data while making such transmission as easy and as comfortable for the patient as possible. To date, the ovoid shape of structure 10 fulfills, inter alia, these requirements.

Figure 2:
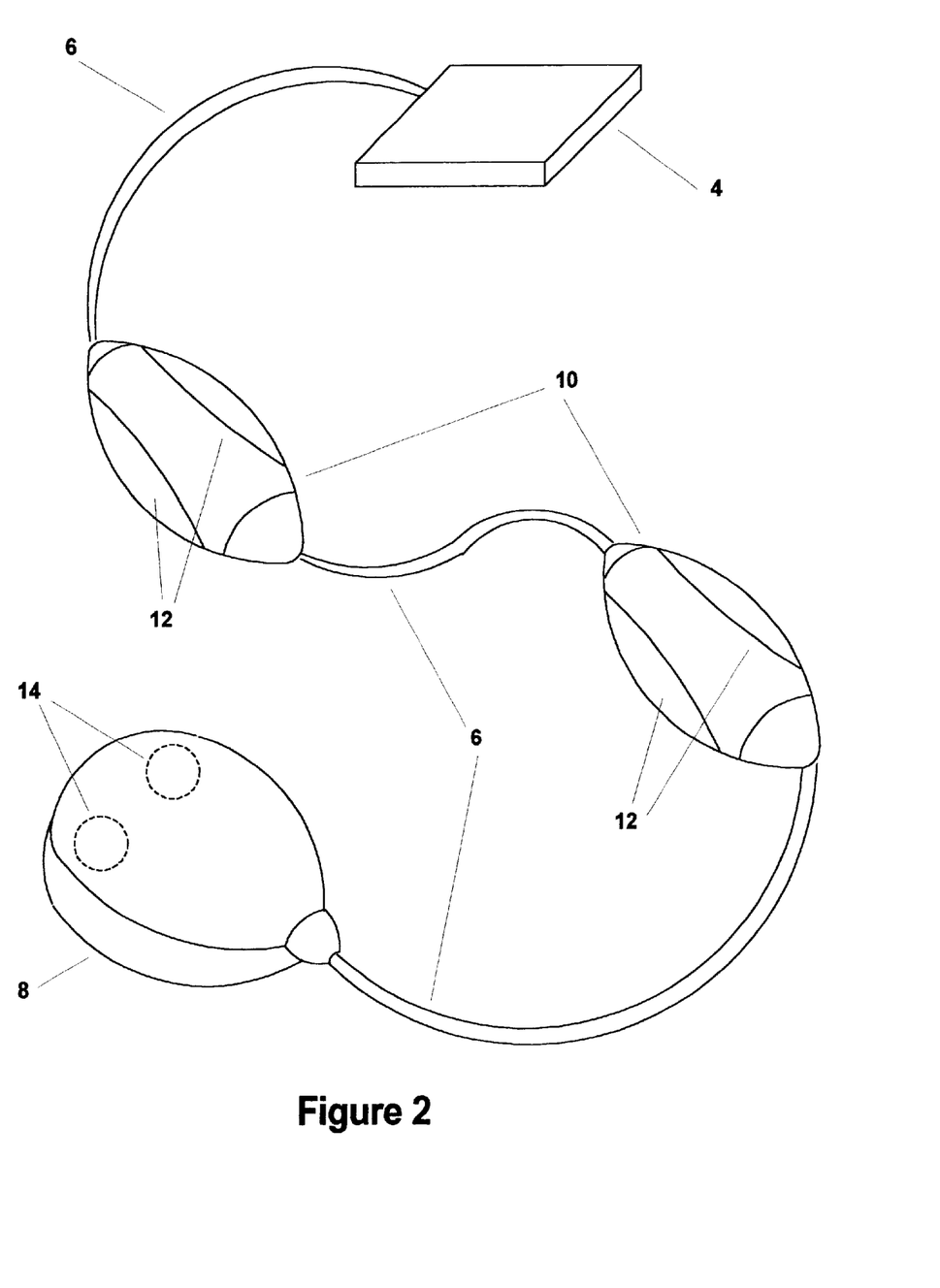
FIG. 2 is an illustration of a second embodiment, with two hand holdable structures connected to a lightweight telemetry head all connected to a cable and an ECG/RF telemetry unit.

FIG. 2 is an illustration of a second embodiment of this invention. In this embodiment, preferably a plurality of structure 10, attached in tandem by cable 6, with one or more conductive non-oxidizing electrodes 12 on their surfaces are shown. To use this device a patient would simply grasp structure 10, one in each hand, and when good skin-electrode contact occurs ECG transmission would begin. Telemetry head 8, is used exclusively to detect and transmit data from the IMD. Telemetry head 8 preferably has no ECG electrodes, only sensors 14. Telemetry head 8 would be held in close proximity to the IMD by an attachment method, such as a pouch or modified sling (not shown). RF transmission of the data via telemetry 4 would begin immediately upon the start of ECG transmission, as described above. Telemetry head 8 could have various shapes and does not need to conform to a grasp because it need not be held by the patient during transmission.

Figure 3A:
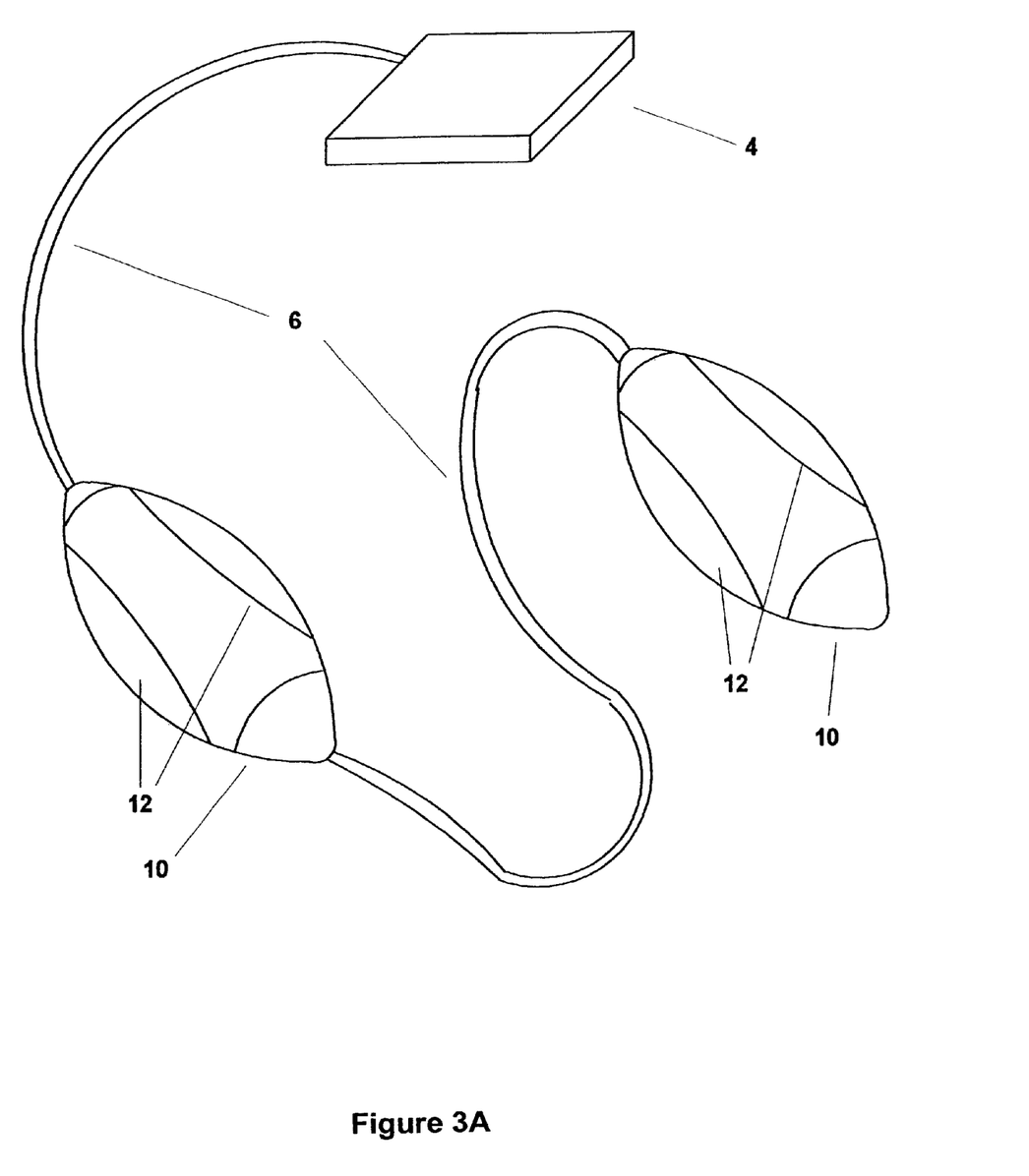
FIG. 3A is an illustration of the third embodiment, that is, with the hand holdable structures connected together by cable and to an ECG/RF telemetry unit.

FIG. 3A illustrates a third embodiment of the present invention in which two of structure 10 are arranged attached in tandem by cable 6 with one or more conductive, non-oxidizing electrodes 12 on their surface. This embodiment is dedicated to acquire ECG tracings via structure 10 and electrodes 12. If data from the IMD were desired, a separate telemetry head (similar to FIG. 1 or 2) would be required.

Figure 3B:
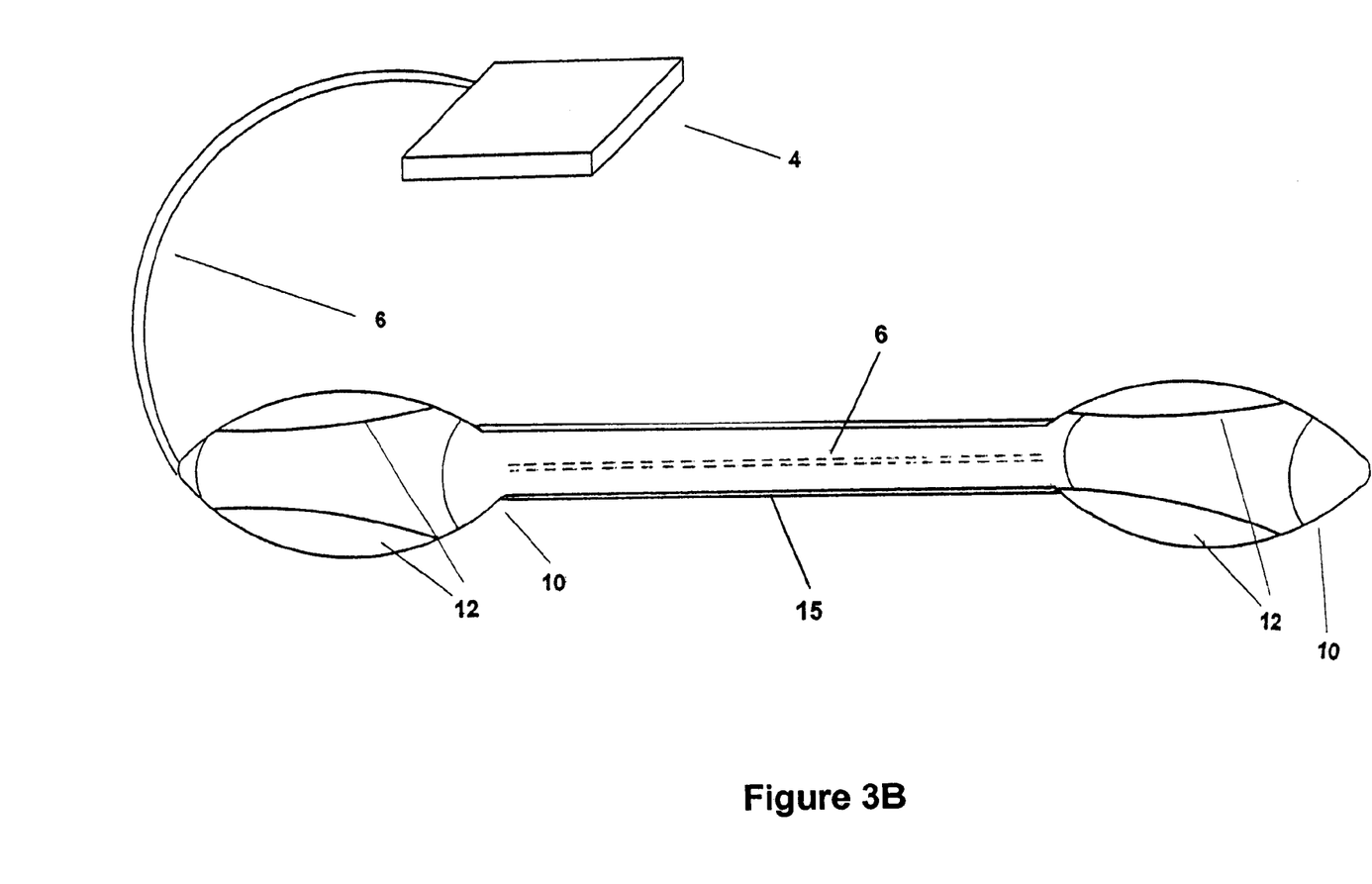
FIG. 3B is an alternate embodiment in which the hand-holdable structure is implemented with a rigid connector.

FIG. 3B is an alternate embodiment in which structures 10 are connected by rigid connector 15 with cable 6 running therethrough.

Figure 4:
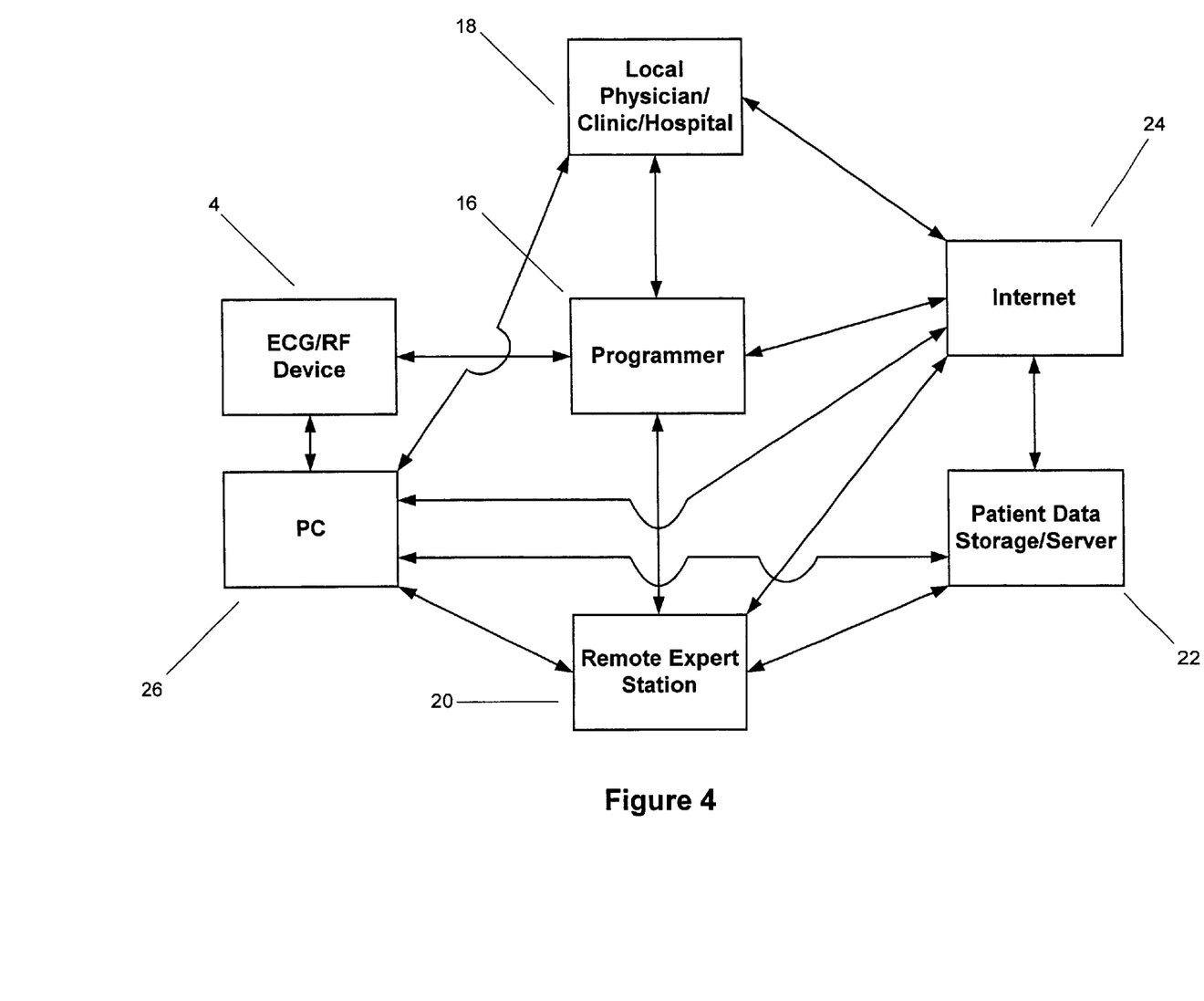
FIG. 4 is a simplified block diagram showing ECG/RF signals for distribution, transfer and management across various medium.

Referring to FIG. 4, the ECG tracing and RF data from the IMD is transmitted from ECG/RF telemetry unit 4 to programmer 16 by any one of several means: hard-wired, RF telemetry, infra-red connectivity, fiberoptics network, Blue Tooth or Home RF technology, transtelephonic, or equivalent. Transmission of the signal from programmer 16 can be via internet/modem connection, telephone landline, satellite telemetry, fiberoptics, laser, or other means as generally described in U.S. Pat. No. 5,752,976 issued to Duffin, et al. and incorporated herein in its totality.

Functionally, an operator at programmer 16 may initiate remote contact. Programmer 16 is adapted too downlink to ECG/RF device 4. Generally, an operator is not needed to operate programmer 16. In fact, uplink from ECG/RF device 4 may be initiated by ECG/RF device 4 and transmission made by any one means as described above. For example, programmer 16 may contain a telemetry transmitter and receiver to uplink and downlink to ECG/RF device 4, a modem, a landline telephone receiver, or equivalent in any case, signal transmission to programmer 16 may occur remotely, that is, from the patient's home, or within the larger confines of a clinic or hospital, e.g., from a waiting room to the room in which the programmer(s) 16 reside. Programmer 16 is preferably of the type disclosed in U.S. Pat. No. 5,345,362 issued to Winkler, et al., incorporated herein in its totality.

Communication between programmer 16 and remote expert station 20 is executed via wave units, as described in the '976 patent. Remote expert station 20 includes a plurality of high speed network web-based or web-compatible communication systems. Preferably, in the context of the present invention, remote expert station 20 is in wireless communication with programmer 16. However, the means of communication between expert station 20 and programmer 16 may be selected from one or a combination of several cable and wireless systems, as mentioned above.

Remote expert station 20 includes software that can identify a noteworthy medical events on the ECG tracing. If such an event is identified, the software determines whether a medical warning is required. If so, warning is immediately issued and transmitted to local physician/clinic/hospital 18 either directly through programmer 16 or indirectly via Internet 24. The event is also recorded in patient data storage 22. In addition, a software in remote expert station 20 analyzes the stored device data and, if necessary, makes a suggestion about programming changes to device parameters. This programming change may be coupled to the medical event that merited a warning. In the alternate, it may be solely based on analysis of stored diagnostic data. For example, if the patient had not attained a normal rate distribution, remote expert station may suggest a change in rate response parameters.

Programmer 16 is also in direct communication with local physician/clinic/hospital 18. As usually practiced, programmer 16 is located within the confines of a "pacing clinic" to use this therapy as an example. The physician may or may not be present at this clinic. If not, the ECG tracings and data may be sent directly to physician 18, responsible for a specific patient.

On the other hand, if, for example, the patient's physician is otherwise occupied at the time of ECG/data acquisition, clinic, or hospital 18 may access remote expert station 20 via Internet 24. If contact by physician/clinic/hospital 18 is further delayed, for example, until the next day, the patient's ECG and other medical data will have already been downloaded to patient data storage 22. In this case, physician/clinic/hospital 18 may access patient data storage 22 via Internet 24.

Patient data storage 22 is a highly interactive component of the system. User identification is required prior to admission. When admitted, the physician 18 may, for example, review the previously mentioned stored suggestions for reprogramming from remote expert station 20. If approved, these programming commands may be routed back to programmer 16 for down linking to the IMD via other methods that are not in the scope of this patent. If not approved, the physician may call for further data that may be obtained by the use of this invention or requesting that the patient come in for a clinic visit.

In one embodiment PC 26 is implemented to transmit/record ECG and IMD data from ECG/RF device 4. PC 26 is adapted to be in data communication with local physician/clinic/hospital 18, remote expert station 20, storage/server 22 and Internet 24.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A hand device devoid of adhesive material and electrically conductive gel material to establish reliable skin-electrode contact for physiological signal acquisition of surface electrocardiogram (ECG), myocardial electrogram (EGM) and pacemaker stimulation signals from a patient, comprising:

a first bulbous structure including at least one surface electrode, said first bulbous structure configured to be easily manually grasped to thereby establish electrical communication between said at least one surface electrode and one hand of a patient;

a second bulbous structure including at least one surface electrode, said second bulbous structure configured to be easily manually grasped to thereby establish electrical communication between said at least one surface electrode and contact in another hand of the patient; and a telemetry unit having operable data communications link with said first bulbous structure and said second bulbous structure, said first bulbous structure operatively electrically connected to said second bulbous structure wherein a temporal physiological surface EGG signals generated between said first and said second bulbous structures is automatically transmitted to said telemetry unit via said data communication link when electrical communication is established for both the first and second bulbous structures.

wherein the telemetry unit includes means for establishing wireless communication with a pacemaker disposed within the patient so that temporal EGM signals from the pacemaker are automatically communicated via the data communications rink when electrical communication is established for both the first and second bulbous structures.

2. The device of claim 1 wherein the means for establishing Wireless communication comprises a headless RF telemetry incorporated into one of said first and second bulbous structures to uplink to the pacemaker.

3. The device of claim 1 wherein a one of said first and second bulbous structures comprises a substantially ovoid shape conforming to a human grasp.

4. The device of claim 3 wherein each said at least one electrode is shaped to conform to said substantially ovoid shape.

5. The device of claim 4 wherein each at least one electrode substantially covers a major surfaces of said substantially ovoid shape.

6. The device of claim 1 wherein said telemetry unit includes a communication link to transmit the surface ECG and the temporal EGM signals to one of: a pacemaker programmer, a personal computer, a remote electronic station, a data server.

7. The device of claim 6 wherein said temporal EGM signals includes historical medical data collected from the pacemaker.

8. A hand-held surface ECG and radio frequency system for detecting cardiac depolarizations for remote monitoring of temporal electrocardiogram (ECG signals and internal cardiac electrogram (EGM) signals from a patient with an implantable medical device (IMD) such as a pacemaker or implantable cardioverter-defibrillator, the system comprising:

a pair of structures operatively electrically coupled together and each of said pair of structures shaped to conform to a manual grasp of a patient;

electrodes incorporated into the pair of structures to enable reliable skin-electrode contact at said grasp of the patent, wherein said contact is established without use of adhesive material or electrically conductive gel material;

a data communication means linking said pair of structures and a radio frequency system for automatically enabling transmission of temporal ECG signals from the pair of structures upon establishment of skin-electrode contact to an external communication device, and wherein said data communication means also automatically transmitting EGM signals from an IMD disposed with in said patient.

9. The system of claim 8 wherein each of said pair of structures comprise substantially ovoid shapes forming a first end and second end rigidly spaced apart by a connecting member.

10. The system of claim 9 wherein said connecting member includes means for routing a data communications cable between said first end and said second end.

11. A method of automatically communicating physiologic signals of a patient to a remote location, comprising:

Initiating a communication link from a pair of structures when each one of said pair of structures is manually grasped in each hand of a patient, said communication link including at least two streams of data, a first data stream comprising surface electrocardiogram (ECG) information and a second data stream comprising internal electrogram (EGM) information generated by an implantable medical device (IMD) disposed within said patient; and terminating the communication link when the manual grasp between at least one of the pair of structures and the patient is interrupted.

12. A method according to claim 11, wherein each of the pair of structures comprise an ovoid shape.

13. A method according to claim 12, wherein at least one surface electrode associated with each of said pair of structures comprises a contoured shaped corresponding to a major surface of each of the pair of structures.

14. A method according to claim 11, wherein the second data stream comprises historical EGM data.

15. A method according to claim 11, wherein the second data stream comprises a temporal trace of cardiac activity, including delivery of pacing therapy.

16. A method according to claim 11, wherein each of the pair of structures comprises a bulbous shape.

17. A method according to claim 11, wherein the second data stream is communicated via a radio frequency link between the IMD and an external telemetry device incorporated into a one of the pair of structures.

18. A method according to claim 17, wherein one of said pair of structures includes a magnetic unit and wherein when said magnetic unit is disposed near the IMD the radio frequency link is established.

* * * * *

UNITED STATES PATENT AND TRADEMARK OFFICE
CERTIFICATE OF CORRECTION

PATENT NO.    : 6,748,260 B2                                     Page 1 of 1
DATED         : June 8, 2004
INVENTOR(S)   : Nelson Au et al.

It is certified that error appears in the above-identified patent and that said Letters Patent is hereby corrected as shown below:

Column 7,
Line 53, delete "wherein each at" and insert -- wherein each side at --.

Signed and Sealed this

Eighteenth Day of January, 2005

JON W. DUDAS
*Director of the United States Patent and Trademark Office*